United States Patent [19]
Bialer et al.

[11] Patent Number: 6,028,102
[45] Date of Patent: Feb. 22, 2000

[54] ANTICONVULSANT DRUGS AND PHARMACEUTICAL COMPOSITIONS THEREOF

[75] Inventors: Meir Bialer; Arie Dagan, both of Jerusalem; Sussan Sherbel, Tarshicha, all of Israel

[73] Assignee: Yissum Research Development Company of the Hebrew University of Jerusalem

[21] Appl. No.: 09/028,911

[22] Filed: Feb. 24, 1998

[51] Int. Cl.$^7$ ....................................... A01N 47/34
[52] U.S. Cl. ............................... 514/489; 560/29
[58] Field of Search .................... 514/529, 616, 514/489; 564/155; 560/148, 29

[56] References Cited

U.S. PATENT DOCUMENTS

| | | |
|---|---|---|
| 4,439,196 | 3/1984 | Higuchi . |
| 4,447,224 | 5/1984 | DeCant, Jr. et al. . |
| 4,447,233 | 5/1984 | Mayfield . |
| 4,475,196 | 10/1984 | La Zor . |
| 4,486,194 | 12/1984 | Ferrara . |
| 4,487,603 | 12/1984 | Harris . |
| 4,925,678 | 5/1990 | Ranney . |
| 4,959,217 | 9/1990 | Sanders et al. . |
| 5,167,616 | 12/1992 | Haak et al. . |
| 5,169,383 | 12/1992 | Gyory et al. . |
| 5,225,182 | 7/1993 | Sharma . |
| 5,585,358 | 12/1996 | Bialer et al. . |

OTHER PUBLICATIONS

Benet and Galeazzi (1979). Non–compartmental determination of steady–state volume of distribution. J. Pharm. Sci. 68:1071–1074.
Bialer, et al (1996 ). Progress report on new antiepileptic drugs a summary of the Third Eilat Conference. Epilepsy Res. 25:299–319.
Bialer, et al (1996 ). Pharmacokinetic analysis and antiepileptic activity of tetramethylcyclopropane analogous of valpromide. Pharm. Res. 13:284–289.
Capobianco et al (1996). An overview of the diagnosis and pharmacologic treatment of migraine. Mayo Clin Proc 71:1055–66.
Chadwich (ed.) New Trends in Epilepsy Management: The Role of Gabapentin. Royal Society of Medicine Services Ltd., London, 1993.
Clark, et al (1995). Remacemide hydrochloride in R.H. Levy, R.H. Mattson and B.S. Meldrun (eds.) Antiepileptic Drugs, 4th ed. Raven Press, pp. 1035–1044.
Conley and Kohn (1987). Functionalized DL–amino acid derivatives. Potent new agent for the treatment of epilepsy. J. Med. Chem. 30:567–574.
Dreifuss (1987). New anticonvulsant drugs in *Epilepsy, Progress in Treatment*, M. Dam. S.I. Johannessen, B. Nilsson and M. Sillapaa (eds.), Wiley & Sons, NY, pp. 247–256.
Freed, et al (1979). Anticonvulsant properties of betaine. Epilepsia. 20:209–213.
Freed (1985). Prevention of strychnine–induced seizures and deaths by the N–methylated glycine derivatives betaine, dimethylglycine and sarcosine. Pharmacol. Biochem. Behav. 22:641–643.
"GABA in Nervous System Function", E. Roberts, T.N. Chase, D.B. Tower (eds.), Raven Press, NY (1976).
Garcia and Altman (1997). Chronic pain states: Pathophysiology and medical therapy. Semin Arthritis Rheum 27:1–16.
Geurts, et al., (1998). N–(Benzyloxycarbonyl) glycine Esters and Amides as New Anticonvulsants. J. Med Chem 41:24–30.
Gibaldi and Perrier (1982). Pharmacokinetics, Ed. 2, Marcel Dekker, New York, pp. 445–449.
Gidal et al (1996). Current developments in neurology, Part I: Advances in the pharamcotherapy of headache, epilepsy and multiple sclerosis. Ann Pharmacother 30(11):1272–6.
Gonzales (1995). Central pain: Diagnosis and treatment strategies. Neurology 45(12 Suppl 9):S11–6; Discussion S35–6.
Guay (1995). The emerging role of valproate in bipolar disorder and other psychiatric disorders. Pharmacotherapy 15(5):631–47.
Hadad and Bialer (1995). Pharmacokinetic analysis and antiepileptic activity of N–valproyl derivates of GABA and glycine. Pharm. Res. 12, 905–910.
Hadad and Bialer (1997). Pharmacokinetic analysis and antiepileptic activity of two new isomers of N–valproyl glycinamide. Biopharm. Drug Disposit. 18:557–566.
Kohn, et al (1988). Marked stereospecificity in a new class of anticonvulsants. Brain Res. 457:371–375.
Kohn, et al (1990). Preparation and anticonvulsant activity of a series of functionalized α–aromatic and α–heteroaromatic amino acids. J. Med. Chem. 33:919–926.
Kohn, et al (1991). Preparation and anticonvulsant activity of a series of functionalized α–heteroatom–substituted amino acids. J. Med. Chem. 34, 2444–2452.

(List continued on next page.)

*Primary Examiner*—Shailendra Kumar
*Attorney, Agent, or Firm*—Kohn & Associates

[57] ABSTRACT

According to the present invention, anticonvulsant compounds N-acetyl,N'-benzylglycinamide and N-benzyloxycarbonylglycinamide-Z-glycinamide are disclosed. The present invention also discloses an anticonvulsant pharmaceutical composition comprising an effective amount of at least one active ingredient selected from N-acetyl,N'-benzylglycinamide and N-benzyloxycarbonylglycinamide-Z-glycinamide and a pharmaceutically acceptable carrier or diluent. The present invention provides a method of controlling convulsions in a mammal by administering to the mammal an effective amount of antiepileptic compounds N-acetyl,N'-benzylglycinamide or N-benzyloxycarbonylglycinamide-Z-glycinamide. Combinations of the anticonvulsion compounds can also be administered. The convulsions may be due to epilepsy, febrile convulsions or convulsions precipitated by irritative lesions in the brain. Further the composition may be used to prevent migraine and to treat chronic pain and bipolar disorder.

6 Claims, 2 Drawing Sheets

OTHER PUBLICATIONS

Krogsgaard–Larsen, et al (1988). Recent advances in GABA agonists, antagonists and uptake inhibitors: Structure activity relationships and therapeutic potential. Advanc. Drug. Res. 17:382–456.

Lambert, et al (1994). Anticonvulsant activities of N–benzyloxycarbonylglycine after parenteral administration. Neuroreport. 5:777–780.

Lambert, et al (1996). Anticonvulsant activity of ester– and amide–type lipid conjugates of glycine and N–benzyloxycarbonylglycine. Eur. J. Pharm. Sci. 4:159–166.

Liu, et al (1990). Potentiation of γ–vinyl GABA (vigabatrin) effects by glycine. Eur. J. Pharmacol. 182:109–115.

McQuay, et al (1995). Anticonvulsant drugs for management of pain: A systemic review. BMJ 311(7012):1047–52.

Mielke (1994). Anticonvulsant therapy for mood disorders. South Med J 87(7):685–8.

Mumford and Canon (1994). Vigabatrin. Epilepsia 35 (Suppl. 5) S25–S28.

Peterson, et al (1990). Potentiation by glycine of anticonvulsant drugs in maximal electroshock seizures in rats. Neuropharmacology, 29:399–409 (1990).

Porter, et al (1984). Antiepileptic drug development program. Cliv. Clin. Quarter. 51:293–305.

Porter (1986). Antiepileptic drugs: efficacy and inadequacy in *New Anticonvulsant Drugs*, B.S. Meldrum and R.J. Porter (eds.), Libbey, London, pp. 3–16.

Post et al (1996). The place of anticonvulsant therapy in bipolar illness. Psychopharmacology (Berl) 128(2):115–29.

Puzantian (1996). Criteria for use of valproate in adult psychiatric inpatients and outpatients. Am J Health Syst Pharm 53(10):1187–8.

Roba et al (1986). Milacemide in "New Anticonvulsant Drug", B.S. Meldrum and R.J. Proter (eds.), Jhon Libny, London, pp. 179–190.

Sachs (1996). Bipolar mood disorder: Practical Strategies for acute and maintenance phase treatment. J Clin Psychopharmacol 16(2 Suppl 1):32S–47S.

Salach, et al (1994). Comparative pharmacokinetic and pharmacodynamic analysis of phthaloyl glycine derivatives with potential antiepileptic activity. Pharm. Res. 11:1429–1434.

Seiler and Sarhan (1984). Synergistic anticonvulsant effects of a GABA agonist and glycine. Gen. Pharmacol. 15:367–369.

Silberstein and Lipton (1994). Overview of diagnosis and treatment of migraine. Neurology 44(10 Suppl 7):S6–16.

Swerdlow (1984). Anticonvulsant drugs and chronic pain. Clin Neuropharmacol 7(1):51–82. [n/a—will mail in].

Toth and Lajtha (1984). Glycine potentiates the action of some anticonvulsant drugs in some seizure models. Neurochem. Res. 8:1711–1718.

Vanvalkenburg et al (1992). New uses of anticonvulsant drugs in psychosis. Drugs 44(3):326–35.

Wood, et al (1988). Amplification by glycine of the effect of the GABA transport inhibitor THPO on synaptosomal GABA level. Neurochem. Res. 13:917–921.

Yamaoka, et al (1978). Statistical moments in pharmacokinetics. J. Pharmacokinet. Biopharm. 6:547–558.

Yamaoka (1986). Methods for pharmacokinetic analysis for personal computers. Edition 2, Nanko–D Led., Tokyo, pp. 145–175. [n/a—will mail in].

ANTICONVULSANT DRUGS AND PHARMACEUTICAL COMPOSITIONS THEREOF

BACKGROUND OF THE INVENTION

1. Field of the Invention

The present invention relates to new anticonvulsants drugs and pharmaceutical compositions containing the anticonvulsants drugs and methods of treating with the drugs.

2. Description of Related Art

GABA is an inhibitory neurotransmitter which plays an important role in the control of neuronal activity in the mammalian central nervous system-CNS [Porter, 1986]. A deficiency in brain GABA levels, has been shown to cause convulsions or epilepsy [Dreifuss, 1987; "GABA (1976)]. Therefore, drugs which increase the amount of GABA available in the brain for neurotransmission have the potential of becoming anticonvulsants and antiepileptic agents. GABA derivatives, such as gamma-vinyl-GABA (GVG) [Mumford and Canon, 1994] and gabapentin [Chadwick (ed), 1993] are two new antiepileptics which have been approved in recent years. Next to GABA, glycine is one of the most important inhibitory neurotransmitter amino acids. Glycine itself does not readily cross the blood-brain barrier due to its zwitterionic character and the absence of an active transport. Similar to GABA, glycine has also been incorporated into the new antiepileptic agent—milacemide [Roba et al, 1986] and remacemide [Clark et al, 1995]. Several reports have shown that co-administration of glycine and other antiepileptics, such as carbamazepine, phenobarbital and GVG, potentiate the anticonvulsant activity in several rats models, due to synergism [Liu et al, 1990; Toth and Lajtha, 1984; Wood et al, 1988; Seiler and Sarhan, 1984; Peterson et al, 1990]. However, neither GABA nor glycine are effective upon oral or systemic administration due to their inability to cross the blood brain barrier (BBB) and their liver metabolic deactivation, which minimizes their availability to the brain [Krogsgaard-Larsen et al, 1988].

Lambert et al. [1994] reported that a glycine derivative N-benzyloxy-carbonylglycine (Z-glycine) was found to be far more active than glycine in rats following chemically and electrically induced seizures. Subsequently, the anticonvulsant activity of ester and amide-type lipid conjugates of glycine and N-benzyloxycarbonylglycine (Z-glycine) were evaluated utilizing the maximal electroshock (MES) and the strychnine tests [Lambert et al, 1996]. In all cases the Z-glycine derivatives were always more potent than the corresponding glycine derivatives with the amide lipid being more active than the ester derivatives [Lambert et al, 1996].

Applicants recently explored the pharmacokinetics and pharmacodynamics (anticonvulsant activity and neurotoxicity) of N-phthaloyl and N-valproyl derivatives of GABA and glycine [Salach et al, 1994; Hadad and Bialer, 1995; U.S. Pat. No. 5,585,358]. Out of the valproyl derivatives only valproyl glycinamide showed a good anticonvulsant activity in both mice and rats due to its better pharmacokinetic profile [Hadad and Bialer, 1995]. N-valproyl glycinamide (TV 1901) is currently undergoing phase I clinical trials [Bialer et al, 1996A]. Subsequently, applicants developed and evaluated analogues and isomers of TV 1901 which showed good anticonvulsant activity in rodents such as tetramethylcyclopropylcarbonyl glycinamide [Bialer et al, 1996B], N-2-enevalproyl glycinamide, valnoctyl glycinamide and diisopropyl acety glycinamide [Hadad and Bialer, 1997]. These four derivatives of TV 1901 showed, in mice and rats, similar anticonvulsant activity and safety margins to that of the parent compound.

However, it would be useful to have additional anticonvulsant compounds since patients can become refractory to one drug over time or have unwanted side effects or reactions (neurotoxicity) when the drugs are being used to control seizures in the patient. Further, about 30% of epileptic patients are not seizure free with the existing antiepileptic drugs. The larger the number of drugs available, the more ability to design an effective individual therapeutic protocol for each patient. Therefore, the current study was designed in order to investigate the anticonvulsant activity, neurotoxicity, and safety margin of a series of amide derivatives of glycinamide (Table 1, compounds I–XI and referred to hereinafter by the roman numeral assigned therein) and to assess the pharmacokinetics of the active compounds. This pharmacokinetic pharmacodynamic relations study led to the discovery of glycinamide derivatives which are, unexpectedly, new anticonvulsant agents as shown herein.

SUMMARY OF THE INVENTION

According to the present invention, anticonvulsant compounds N-acetyl,N'-benzylglycinamide and N-benzyloxycarbonylglycinamide-Z-glycinamide are disclosed. The present invention also discloses an anticonvulsant pharmaceutical composition comprising an effective amount of at least one active ingredient selected from N-acetyl,N'-benzylglycinamide and N-benzyloxycarbonylglycinamide-Z-glycinamide and a pharmaceutically acceptable carrier or diluent. The convulsions may be due to epilepsy, febrile convulsions, or convulsions precipitated by irritative lesions in the brain.

The present invention also provides a method of controlling epileptic seizures, febrile convulsions, or convulsions precipitated by irritative lesions in the brain of a mammal, by administering to the mammal, an effective amount of at least one of anticonvulsant compounds N-acetyl,N'-benzylglycinamide or N-benzyloxycarbonylglycinamide-Z-glycinamide. Combinations of the anticonvulsant compounds can also be administered.

The present invention also provides a method of controlling migraine, chronic pain, and psychiatric disorders such as bipolar mood disorder in a mammal by administering to the mammal an effective amount of at least one of the anticonvulsant compounds N-acetyl,N'-benzylglycinamide or N-benzyloxycarbonylglycinamide-Z-glycinamide. Combinations of the anticonvulsant compounds can also be administered.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
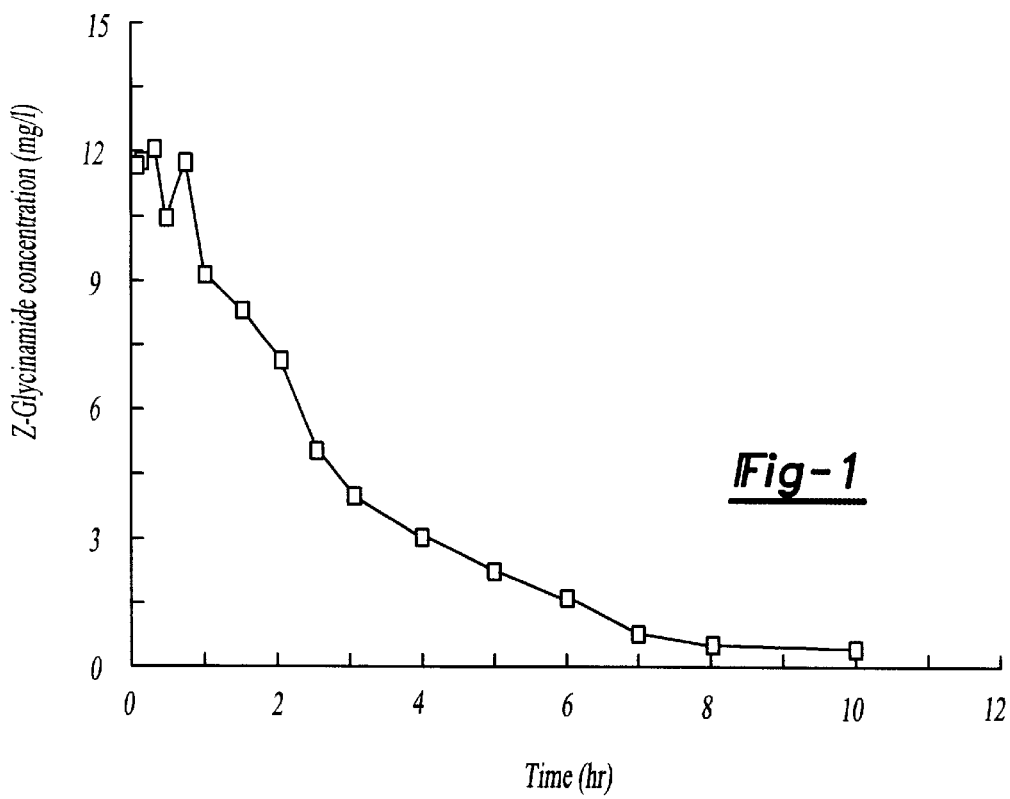
FIG. 1 is a graph showing the mean plasma levels of N-acetyl,N'-benzylglycinamide (VII) obtained following its iv administration (400 mg) to six dogs.

According to the present invention, anticonvulsant compounds N-acetyl,N'-benzylglycinamide and N-benzyloxycarbonylglycinamide-Z-glycinamide are disclosed (Table 1, formulae VII and IX respectively).

A method of controlling epileptic seizures in a mammal by administering to the mammal an effective amount of antiepileptic compounds N-acetyl,N'-benzylglycinamide or N-benzyloxycarbonylglycinamide-Z-glycinamide or combinations thereof is also disclosed. The seizures to be treated include generalized and partial seizures, in addition other forms of seizures seen in epilepsy, including absence seizures can be treated. In an embodiment, the mammal to be treated is human but other mammalian species can be treated in veterinary applications.

The present invention also discloses an anticonvulsant pharmaceutical composition, comprising an effective amount of at least one active ingredient selected from N-acetyl,N'-benzylglycinamide and N-benzyloxycarbonylglycinamide-Z-glycinamide and a pharmaceutically acceptable carrier or diluent. Combinations of these two anticonvulsant compounds may be formulated in the pharmaceutical composition of the present invention as the active ingredient.

The compounds of the present invention may also be administered in combination with other antiepileptic and/or anticonvulsant drugs as needed to provide seizure control.

In addition to epilepsy, the anticonvulsant compounds of the present invention can be used to control febrile convulsions and also convulsions which can be precipitated by an irritative lesion such as metastatic brain disease, stroke and Multiple Sclerosis. For febrile convulsions, the anticonvulsants are administered when the patient has a high fever and there is a previous history of at least one febrile convulsion or a family history of febrile convulsions. For convulsions due to an irritative lesion in the central nervous system, the anticonvulsants are also administered if there is a previous history of convulsions in the patient. Further, for metastatic brain disease, the anticonvulsant can be administered during radiation therapy as is known in the art.

Further, the compounds of the present invention can be used to treat psychiatric disorders such as bipolar disease and affective disorders, migraine (generally as a preventive), and chronic pain disorders as is known in the art. The compounds of the present invention may be administered with other anticonvulsant compounds in therapeutic protocols in the treatment of these diseases as is known in the art. [Capobianco et al., 1996; Garcia and Altman, 1997; Gidal et al, 1996; Gonzales, 1995; Guay, 1995; McQuay et al, 1995; Mielke, 1994; Post et al, 1996; Puzanatian, 1996; Sachs, 1996; Silberstein and Lipton, 1994; Swerdlow, 1984; Van-Valkenburg et al, 1992]. As is shown in Example 2 herein below the compounds of the present invention cross the blood-brain-barrier readily and therefore have the capacity to be used in ability to be used in these conditions.

The effective amounts of the anticonvulsant compounds of the present invention are determined on a species basis, and are administered and dosed in accordance with good medical practice, taking into account the disease or syndrome being treated, clinical condition of the individual patient, the site and method of administration, scheduling of administration, patient age, sex, body weight, and other factors known to medical practitioners. The pharmaceutically "effective amount" for purposes herein is thus determined by such considerations as are known in the art. The amount must be effective to achieve at least a 10% reduction, but preferably a 50% reduction, in seizure/convulsant counts for those patients being treated for convulsions, and changes in psychiatric profiles for those patients being treated for psychiatric disorders, and a reduction in migraine frequency or pain intensity in patients with those disorders. In particular see generally the reference text "Antiepileptic Drugs" (4th edition. R. H. Levy et al (eds) Raven Press, 1995) for methodology on use and dosage of such drugs and means to determine effective amounts and see as well Capobianco et al., 1996; Gonzales, 1995; Puzanatian, 1996; Sachs, 1996; Silberstein and Lipton, 1994 for migraine, chronic pain and psychiatric disorder treatment. It should be noted that often anticonvulsant drugs must be tittered to the correct dosage, particularly a maintenance dosage, for the individual patient as is known in the art.

In the method of the present invention, the N-acetyl,N'-benzylglycinamide and N-benzyloxycarbonylglycinamide-Z-glycinamide (i.e., N-acetyl,N'-benzylglycinamide (VII) and Z-glycinamide (IX)) can be administered in various ways. It should be noted that the compounds can be administered as the compound or as pharmaceutically acceptable salt. It can also be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques depending on the drug target and patient status. Topical applications, suppositories and implants of the compounds are also useful. The patient being treated is a warm-blooded animal and, in particular, mammals including man. The pharmaceutically acceptable carriers, diluents, adjuvants and vehicles as well as suppository and implant carriers generally refer to inert, non-toxic solid or liquid fillers, diluents or encapsulating material not reacting with the active ingredients of the invention nor changing the biological activity of the compounds of the present invention.

It is noted that humans are treated generally longer than the animals exemplified herein which treatment has a length proportional to the length of the disease process and drug effectiveness. The doses may be single doses or multiple doses per day, but single daily doses are preferred. The doses will generally be tittered down to the lowest possible dose to sustain reduced convulsions. Optimal dosing schedules may be calculated using measurements of drug accumulation in the body. Practitioners of ordinary skill in the art can readily determine delivery routes, optimum dosages, dosing methodologies, and repetition rates. Optimum dosages may vary depending on the relative potency of N-acetyl,N'-benzylglycinamide and N-benzyloxycarbonylglycinamide-Z-glycinamide, and can generally be determined based on $ED_{50}$ values in in vitro and in vivo animal studies and clinical trials as shown in the Examples.

When administering the N-acetyl,N'-benzylglycinamide and N-benzyloxycarbonylglycinamide-Z-glycinamide (i.e., (VII) and (IX)) parenterally, the compounds will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, pall (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

Topical administration can be effected by any method known in the art and can include incorporation of the pharmaceutical composition into creams, ointments or transdermal patches.

A pharmacological formulation of the N-acetyl,N'-benzylglycinamide and N-benzyloxycarbonylglycinamide-Z-glycinamide can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the N-acetyl,N'-benzylglycinamide and N-benzyloxycarbonylglycinamide-Z-glycinamide utilized in the present invention can be administered orally to the patient. Conventional methods such as administering the compounds in tablets, suspensions, solutions, emulsions, capsules, powders, syrups and the like are usable.

Known techniques which deliver the N-acetyl,N'-benzylglycinamide and N-benzyloxycarbonylglycinamide-Z-glycinamide ((VII) and (IX)) orally, topically, subcutaneously or parenterally including intravenous, intraarterial, intramuscular, intraperitoneally, and intranasal administration as well as intrathecal and infusion techniques and retain the biological, therapeutic activity are preferred.

In one embodiment, the compounds may be administered initially by intravenous injection to bring blood levels of the compounds of the present invention to a suitable level. The patient's N-acetyl,N'-benzylglycinamide and N-benzyloxycarbonylglycinamide-Z-glycinamide levels are then maintained by an oral dosage form, although other forms of administration, dependent upon the patient's condition and as indicated above, can be used. The quantity of compounds to be administered will vary for the patient being treated and will vary from about 100 ng/kg of body weight to 100 mg/kg of body weight per day and in one embodiment will be from 10 µg/kg to 10 mg/kg per day.

The present invention provides in the Examples a pharmacokinetic analysis of N-acetyl,N'-benzylglycinamide (VII) and Z-glycinamide (IX) in dogs that shows that these two compounds have similar pharmacokinetic parameters. Compounds VII and IX have the following mean (±SD) pharmacokinetic parameters, respectively: CL–6.8±0.84 L/h and 10.7±4.3 L/h; $V_{SS}$–21±4L and 33±10 L; $t_{1/2}$–2.1±0.5 h and 2.3±1.3 h and MRT–3.0±0.6 h and 3.3±1.8 h. The mean fraction excreted unchanged ($f_e$) in the urine of compound VII was 9.8±5.4% and the $f_e$ value of Z-glycinamide was 2.3±1.3%. Both compounds are eliminated from the body mainly by metabolism which probably occurs primarily in the liver. Therefore, their hepatic extraction ratio (E) is 1.25 and 2% respectively indicating that these compounds will not undergo liver first pass effect or hepatic presystemic metabolism upon oral administration, in comparison to other glycinamide derivatives (Table 3) such as phthaloyl glycinamide [Salach et al, 1994] and N-valproyl glycinamide [Hadad and Bialer, 1995]. Z-glycine (VIII) has a similar CL value but its $V_{SS}$ was the lowest (0.2 L/kg) and therefore its $t_{1/2}$ was the shortest. As Z-glycinamide was mainly metabolized to the inactive Z-glycine it indicates that the parent compound is the active entity.

The other four compounds tested in the Examples have a low CL, a volume of distribution of about 1–2.3 L/kg and a mean half-life of more than two hours. The better pharmacokinetic profile of compounds VII and IX appear to contribute to their anticonvulsant activity and the lack of activity of Z-glycine (VIII).

Kohn et al [1988; 1990] demonstrated that N-acetyl,N'-benzyl DL-phenyl glycinamide and N-acetyl,N'-benzyl DL-alaninamide have a marked anticonvulsant activity in the MES test in mice. For both compounds the anticonvulsant activity was due to the D-stereoisomer as the L-stereoisomer was virtually inactive. An analogous compound N-acetyl,N'-benzylglycinamide (VII) was found to be active at a higher dose of 300 mg/kg [Conley and Kohn, 1987]. Heterocyclic derivatives such as (R,S)-2-acetamido-N-benzyl-2-pyrolacetamide were more potent than the analogous alanine and phenylglycine derivatives [Kohn et al, 1990; 1991]. From the above SAR study, the applicants concluded that stringent stearic and electronic requirements exist for obtaining maximal anticonvulsant activity in this class of amino acid derivatives. Unlike glycine, the N-methylated glycine derivatives betaine (N,N,N-trimethyl glycine), dimethylglycine and sarcosine (N-methylglycine) antagonized in mice, strychnine-induced seizures [Freed, 1985]. Betaine was also found to block the induction of convulsions by electroshock, metrazole and homocysteine [Freed et al, 1979].

Out of the compounds investigated in this study and shown in the Examples all dipeptides (compounds I–III, VI, X and XI) were found to be inactive as anticonvulsant. The only two active compounds that emerged from this study were lipophilic derivatives of glycinamide (compounds VII and IX) which demonstrated similar pharmacokinetic profiles.

The major pharmacokinetic parameters of compounds VII and IX were similar to that of other active glycinamide derivatives, phthaloylglycinamide and N-valproyl glycinamide [Salach et al, 1994; Hadad and Bialer, 1995].

The basis for the lack of anticonvulsant activity of the dipeptide derivatives and the activity of compounds VII and IX is due to either their pharmacodynamic property or pharmacokinetic profile or perhaps a combination of both. Unlike Lambert et al. [1994] Z-glycine was found to be inactive in this study. However, unexpectedly its glycinamide analogue (IX) was found to be active and possess better pharmacokinetic properties.

The above discussion provides a factual basis for the use of anticonvulsant compounds N-acetyl,N'-benzylglycinamide and N-benzyloxycarbonylglycinamide-Z-glycinamide (VII and IX). The methods used with and the utility of the present invention can be shown by the following non-limiting examples and accompanying figures.

EXAMPLES

Methods

Preparation of Compounds to be Tested

N-benzyloxycarbonyl glycine-Z-glycine (VIII), N-benzyloxycarbonyl glycylglycine (X), N-acetylglycine (IV), N-acetylglycinamide (V) and Boc-glycine were purchased from the Aldrich Chemical Company (Milwauke, Wis., U.S.A.). Z-glycinamide (IX), glycylglycine, Z-GABA, dicyclohexyl-carbodiimide (DCC) and 1-ethyl-3(3-dimethyldiaminopropyl) carbodiimide (EDC) were purchased from Sigma Chemical Company (St. Louis, Mo.). The chemical structure of the glycine and glycinamide derivatives investigated in this study are presented in Table 1. Compounds II, III, VI, VII, and XI were prepared according to the following respective methods.

Glycylglycinamide (II)

To a solution of 2 g (11.4 mmole) of N-(tert-butoxycarbonyl)-glycine (Boc-glycine) and 1.26 g (22.8 mmole) of glycinamide hydrochloride in 100 mL of DMF at neutral pH, 3.54 g (17.1 mmole) of dicyclohexylcarbodiimide (DCC) was added and 0.28 g (2.3 mmole) of 4-dimethylaminopyridine (DMAP) was added as a catalyst. The reaction mixture was stirred for 24 hours at room temperature, the insoluble materials were filtered and the filtrate was evaporated to dryness in vacuum.

The residue was dissolved in 100 mL of the mixture dichloromethane—TFA (8:2 respectively), the mixture was stirred for 2 hours to remove the Boc group and the mixture was concentrated in vacuum leaving an oil product. The oil product was dissolved in 100 mL of hydrochloric acid solution (0.1 N), washed 4 times with 100 mL of dichloromethane, and the water fraction was evaporated to dryness in vacuum. The product was recrystallized from methanol-ethylacetate (2:8 respectively) to get 0.95 g (5.7 mmole) of the dipeptide as a hydrochloride salt, yield of 50%, m.p.: 177–180° C.

Anal. Calculated for $C_4H_9N_3O_2$: Calculated: C: 28.65% H: 6% N: 25% Found: C: 28.65% H: 5.7% N: 23.8%

$^1$H NMR ($D_2O$): 3.747 (s, 2H, $CH_2$), 3.844 (s, 2H, $CH_2$) ppm.

Gaboylglycinamide (III)

The same procedure as for glycylglycinamide (II) was used to prepare gaboylglycinamide by using Boc-GABA, yield of 55%, m.p: 155–157° C.

Anal. Calculated for $C_6H_{14}N_3O_2$: Calculated: C: 36.82% H: 7.08% N: 21.26% Found: C: 36.52% H: 6.99% N: 21.19%

$^1$H NMR ($D_2O$): 3.85 (s, 2H, $CH_2$), 3.62 (T, 2H, $CH_2$) 2.42 (T, 2H, $CH_2$), 2.12 (Q, 2H, $CH_2$) ppm.

N-Acetylglycylglycinamide (VI)

N-Acetylglycine (5 g, 43 mmole) and 9.5 g (86 mmole) of glycinamide hydrochloride were dissolved in a 150 mL of a mixture of water-acetonitrile (50:50), 8.65 g (86 mmole) of triethylamine (TEA) and 12.6 g (64 mmole) of 1-ethyl-3(3-dimethyl aminopropyl)carbodiimide (EDC) as a coupling reagent were added to the mixture and the mixture was refluxed for 12 hours. The mixture was left to cool at room temperature, the insoluble materials were filtered and the filtrate was evaporated to dryness in vacuum. The residue was recrystallized from a big fraction of acetonitrile to get a mixture of the product with the salt TEA:HCl, the solid crystals were dissolved in distilled water and purified from the salt by a strong cation exchange chromatography (120 plus). The water fractions were collected and the water was removed by lyophilization to get a pure product 4.5 g (26 mmole), yield of 60%.

Anal. Calculated for $C_6H_{11}N_3O_3$: Calculated: C: 41.62% H: 6.36% N: 24.27% Found: C: 41.90% H: 6.34% N: 23.9%

$^1$H NMR ($D_2O$): 3.919 (s, 2H, $CH_2$), 3.896(s, 2H, $CH_2$), 2.037 (s, 3H, $CH_3$) ppm.

N-Acetyl,N'-benzylglycinamide (VII)

N-acetylglycine (5 g, 43 mmole) and 8.4 g (86 mmole) of benzylamine were dissolved in 150 mL of a mixture of water-acetonitrile and two equivalents of EDC (1-ethyl-3(3-dimethyl aminopropyl) carbodiimide) were added as a coupling reagent and the mixture was refluxed for 6 hours. The mixture was left to cool at room temperature, the insoluble material was filtered and the filtrate was evaporated to dryness in vacuum. The dry residue was dissolved in 200 mL of hydrochloric acid solution (0.1 N) and extracted 4 times with 100 mL of dichloromethane and the fractions of dichloromethane were collected, dried and evaporated to dryness. The product was recrystallized from ethylacetate to get a pure product 6.2 g (30 mmole), yield of 70%.

Anal. Calculated for $C_{11}H_{14}N_2O_2$: Calculated: C: 62.05% H: 7.17% N: 14.35% Found: C: 62.13% H: 7.15% N: 14.23%

$^1$H NMR ($CDCl_3$): 7.3 (M, 5H, Ar), 6.58(br,s, 1H, NH), 6.78 (br,s, 1H, NH), 4.41 (D, 2H, $CH_2$), 3.93 (D, 2H, $CH_2$), 2.05 (s, 3H, $CH_3$) ppm.

N-Benzyloxycarbonyl Glycylglycinamide (XI)

N-benzyloxycarbonylglycine (3 g, 14.4 mmole) were dissolved in 200 mL of dichloromethane and 4.5 g (21.6 mmole) of DCC were added. The mixture was stirred at room temperature for 2 hours, the insoluble materials were removed and 3.2 g (28.8 mmole) of glycinamide hydrochloride and 2.93 g (28.8 mmole) of TEA (triethylamine) were added to the filtrate. The reaction was stirred for 24 hours at room temperature, the insoluble materials were filtered and the filtrate was evaporated to dryness in vacuum. The residue was recrystallized from distilled water to get a pure product 1.9 g (7.2 mmole), yield of 50%.

Anal. Calculated for $C_{12}H_{15}N_3O_4$: Calculated: C: 54.34% H: 5.66% N: 15.85% Found: C: 54.54% H: 5.66% N: 15.95%

$^1$H NMR ($CD_3OD$): 6.1 (M, 5H, Ar), 3.75(s, 2H, $CH_2$), 2.5 (s, 2H, $CH_2$), 2.42 (s, 2H, $CH_2$) ppm.

Animals Used in the Tests

The experiments were carried out on six male dogs (mongrels), ranging in weight between 18 and 22 kg. In a randomized cross over design, each dog was injected intravenously (in 1.5 mL of DMSO) with a dose of 400 mg of N-acetyl,N'-benzylglycinamide (VII), 404 mg (on dose equivalent to 400 mg of compound VII) of Z-glycinamide (IX) and 406 mg of Z-glycine (VIII). Urine was collected systematically for 12 hours after dosing, by means of an indwelling catheter.

Test Protocol

Venous blood samples (6 mL) were collected via an indwelling catheter (from the cephalic vein) at specified intervals following injection (0, 5, 10, 20, 30, 45 minutes and 1, 1.5, 2, 2.5, 3, 4, 5, 6, 7, 8, 10 and 12 hours respectively). The plasma was then immediately separated by centrifugation at 3000 g for 15 minutes and stored at −20° C. Before each assay, the plasma was allowed to reach room temperature, vortexed, centrifuged and the residual clot removed.

Urine samples were collected via a urine catheter at specified intervals following injection (0, 1, 2, 3, 4, 5, 6, 7, 8, 9, 10 and 12 hours respectively), the samples volume were measured and the urine samples were stored at −20° C. Plasma and urine levels of compounds VII, VIII and IX were then assayed by a HPLC assay described herein below.

HPLC Assay for Monitoring N-acetyl,N'-benzylglycinamide (VII) and N-benzyloxycarbonylglycinamide (IX) in Dog Plasma and Urine Plasma samples are allowed to reach room temperature, vortexed and centrifuged. The plasma was then assayed as follows:

To 0.5 mL of plasma, 10 $\mu$g of an internal standard (N-benzyl-oxycarbonylglycinamide (IX)) and 4 mL of tert-butylmethylether were added. The mixture was vigorously vortexed for 30 seconds, centrifuged for 10 minutes at 3000 g, the organic phase was separated and evaporated to dryness (using a vortex evaporator). To the residue, 80 $\mu$l of methanol were added, the mixture was vortexed and 30 $\mu$l were injected into the HPLC (Schimadzu SCL-10A with a UV-visible detector model SPD-10A).

Urine samples are allowed to reach room temperature, vortexed and centrifuged. The urine was then assayed as follows:

To 0.25 mL of urine, 10 $\mu$g of internal standard (N-benzyl-oxycarbonylglycinamide (IX)), 100 $\mu$l of hydrochloric acid solution (1 N) and 4 mL of tert-butylmethylether were added. The mixture was vigorously vortexed for 30 seconds and centrifuged for 10 minutes at 3000 g, the organic phase was separated and transferred to another test tube containing 0.5 mL of sodium hydroxide solution (1N), the mixture was vigorously vortexed for 30 seconds, centrifuged for 10 minutes at 3000 g, the organic phase was separated and evaporated to dryness (using a vortex evaporator). To the residue, 80 $\mu$l of methanol were added, the mixture was vortexed and 30 $\mu$l were injected into the HPLC.

HPLC conditions: HPLC column; Hypersil ODS (C-18) 5$\mu$, 4.6×150 mm; Wavelength: 258 nm; Mobile phase: 60% water, 40% methanol and 0.01% trifluoroacetic acid.

The same assay was used for monitoring N-benzyloxycarbonyl-glycinamide (IX) in dog plasma and dog urine using N-acetyl,N'-benzylglycinamide as an internal standard.

HPLC Assay for Monitoring Z-glycine (VIII) in Dog Plasma and Urine

Plasma samples are allowed to reach room temperature, vortexed and centrifuged. The plasma was then assayed as follows:

To 0.5 mL of plasma, 10 $\mu$g of internal standard (Z-GABA), 100 $\mu$l of hydrochloric acid solution (1N) and 5 mL of tert-butylmethylether were added. The mixture was vigorously vortexed for 30 seconds, centrifuged for 10 minutes at 3000 g, the organic phase was separated and evaporated to dryness (using a vortex evaporator). To the residue, 100 $\mu$l of mobile phase were added, the mixture was vortexed and 30 $\mu$l were injected to the HPLC.

Urine samples was allowed to reach room temperature, vortexed and centrifuged. The urine was then assayed as follows:

To 0.1 mL of urine, 30 $\mu$g of internal standard (Z-GABA) and 5 mL of tert-butylmethylether were added. The mixture was vigorously vortexed for 30 seconds, centrifuged for 10 minutes at 3000 g, the organic phase was separated off. To the aqueous phase, 0.5 mL of heptane sulfonic acid solution (0.5% w/v) and 5 mL of tert-butylmethylether were added. The mixture was vigorously vortexed for 30 seconds, centrifuged for 10 minutes at 3000 g, the organic phase was separated and evaporated to dryness (using a vortex evaporator). To the residue, 100 $\mu$l of mobile phase were added, the mixture was vortexed and 30 $\mu$l were injected to the HPLC.

HPLC conditions: HPLC column: Lichrocart 250-4, Lichrosphere 100 RP-18, 5$\mu$; Wavelength: 258 nm; Mobile phase: 60% buffer acetate (pH=3), 40% methanol.

A linear response was observed for compounds VII and IX at a concentration range of 2 to 40 mg/L and for compound VIII at a concentration range of 2 to 80 mg/L. The interday percentage coefficient of variation (% CV) among replicates ranged between 2.6 to 11.1% for N-acetyl,N'-benzylglycinamide (VII), 3.2 to 11.5% for Z-glycine (VIII) and 2.7 to 10.5 for Z-glycinamide (IX) with 18.4% CV at lowest limits of quantification (LOQ) of 2 mg/L only for Z-glycinamide.

Screening of Anticonvulsant Activity

Compounds I–XI were screened in carworth farm #1 mice (ip—in a volume of 0.01 mL/g of body weight) and sprague-Dawley rats (po—in a volume of 0.004 mL/g of body weight) for their anticonvulsant activity and neurotoxicity by the NIH epilepsy Branch [Porter et al, 1984]. The screening procedure involved the following:

1) the maximal electroshock (MES) test, which measures seizure spread; 2) the subcutaneous pentylenetetrazol test (sc Met test) which measures seizure threshold; and 3) the rotored ataxia test which assesses neurotoxicity.

Pharmacokinetic Analysis

The linear terminal slope ($\beta$) of log C (drug plasma concentration of compounds VII, VIII or IX) versus t (time) was calculated by the method of least squares. The terminal half-life of each compound ($t_{1/2}\beta$) was calculated from the quotient 0.69/terminal slope. The AUC (area under the C versus t curve) was calculated by using the trapezoidal rule with extrapolation to infinity. The total body clearance (CL) of the investigated compounds was calculated by using the quotient of the iv dose (D) and the AUC. The volume of distribution ($V_\beta$) was calculated using the quotient of the clearance and the linear terminal slope. The volume of distribution at steady state ($V_{SS}$) and the mean residence time (MRT) were calculated by standard methods [Gibaldi and Perrier, 1982; Benet and Galeazzi, 1979; Yamaoka, et al, 1978; Yamaoka, 1986].

The fraction metabolized ($f_m$) of Z-glycinamide (IX) to Z-glycine (VIII) was calculated from the quotient of AUCs of Z-glycine (VIII) as a metabolite of Z-glycinamide (IX) to the AUC of Z-glycine obtained after its iv administration to the same dogs.

The fraction excreted unchanged ($f_e$) of compounds VII, VIII and IX was calculated from the ratio of the cumulative amount excreted unchanged in the urine (U) to the dose.

Partitioning and Stability Studies

The blood-plasma concentration ratio of compounds VII and IX (partitioning study) was carried out at room temperature (25° C.) by spiking known amounts of the compound in six samples of fresh blood taken from a dog prior to drug administration. N-acetyl, N'-benzylglycinamide and Z-glycinamide concentrations were 5, 10, 15, 20, 30 and 40 mg/L. Each blood sample was centrifuged immediately after spiking and the separation of the plasma was carried out according to the procedure described hereinabove. Plasma levels of the two compounds VII and IX were determined by HPLC.

A blood stability study of compounds VII and IX was carried out by incubating 600 μg of each compound in 30 mL of dog blood (placed in heparinized test tube) at 37° C. with continuous shaking. Blood samples (4 mL) were then collected at the following times: 0, 1, 2, 3, 4, 5 and 6 hours. Plasma was immediately separated and the compounds concentrations in the plasma assayed by HPLC.

Example 1

Stability studies showed that compound VII was unstable in dog blood for 6 hours at physiological conditions. Compound IX was stable in dog blood for 6 hours at physiological conditions. Subsequently, the stability of compound VII was tested in dog blood at 20° C. The results showed that compound VII was unstable at 20° C. in dog blood, and was stable at 37° C. and 20° C. in dog plasma.

Compounds VII and IX were evenly distributed between blood and plasma with a plasma to blood ratio of 0.87±11 and 0.95±0.05 respectively.

Table 1 describes the glycine and glycinamide derivatives investigated in this study. The dipeptides: glycylglycine (I), glycylglycinamide (II) and gaboylglycinamide (III) did not show anticonvulsant activity following ip administration (300 mg) to mice. Applicants therefore decided to derivatize glycinamide and the above dipeptides by synthesizing their N-acetyl and N'-benzyl derivatives (compounds IV–VIII). Out of the derivatized compounds (compounds IV–VIII), only N-acetyl,N'-benzyl glycinamide (VII) showed anticonvulsant activity following ip administration of 100 mg/kg to mice. Compound VII did not show neurotoxic signs at a dose as high as 300 mg/kg. Therefore, this compound was further analyzed quantitatively and its $ED_{50}$ data and protective indices in comparison to phthaloyl glycinamide [16] and valproyl glycinamide—TV 1901 [17] are presented in Table 2. N-benzyloxycarbonylglycinamide (IX) also showed anticonvulsant activity in mice and its $ED_{50}$ values are presented in Table 2. As a consequence of their anticonvulsant activity, the pharmacokinetics of compounds VII and IX were investigated following iv administration (400 mg) to six dogs, and the mean plasma levels of compounds VII and IX are presented in FIGS. 1 and 2, respectively.

Figure 2:
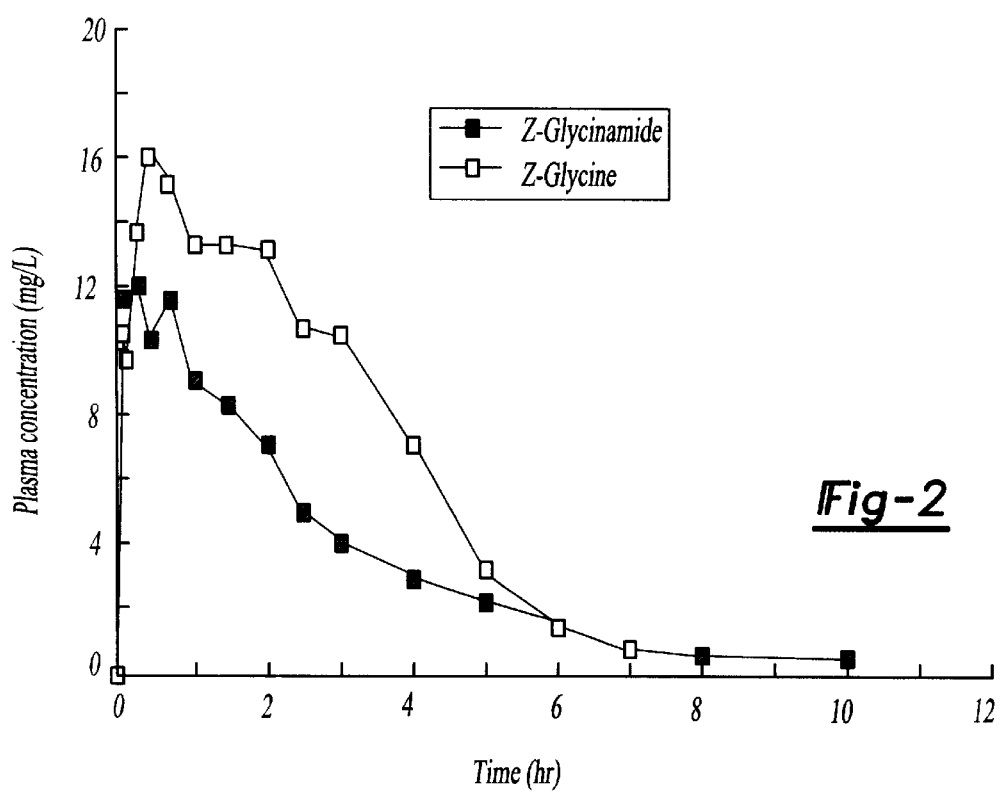
FIG. 2 is a graph showing the mean plasma levels of N-benzyloxycarbonylglycine (VIII) and N-benzyloxycarbonylglycinamide (IX) following iv administration of N-benzyloxycarbonylglycinamide to six dogs.
Figure 3:
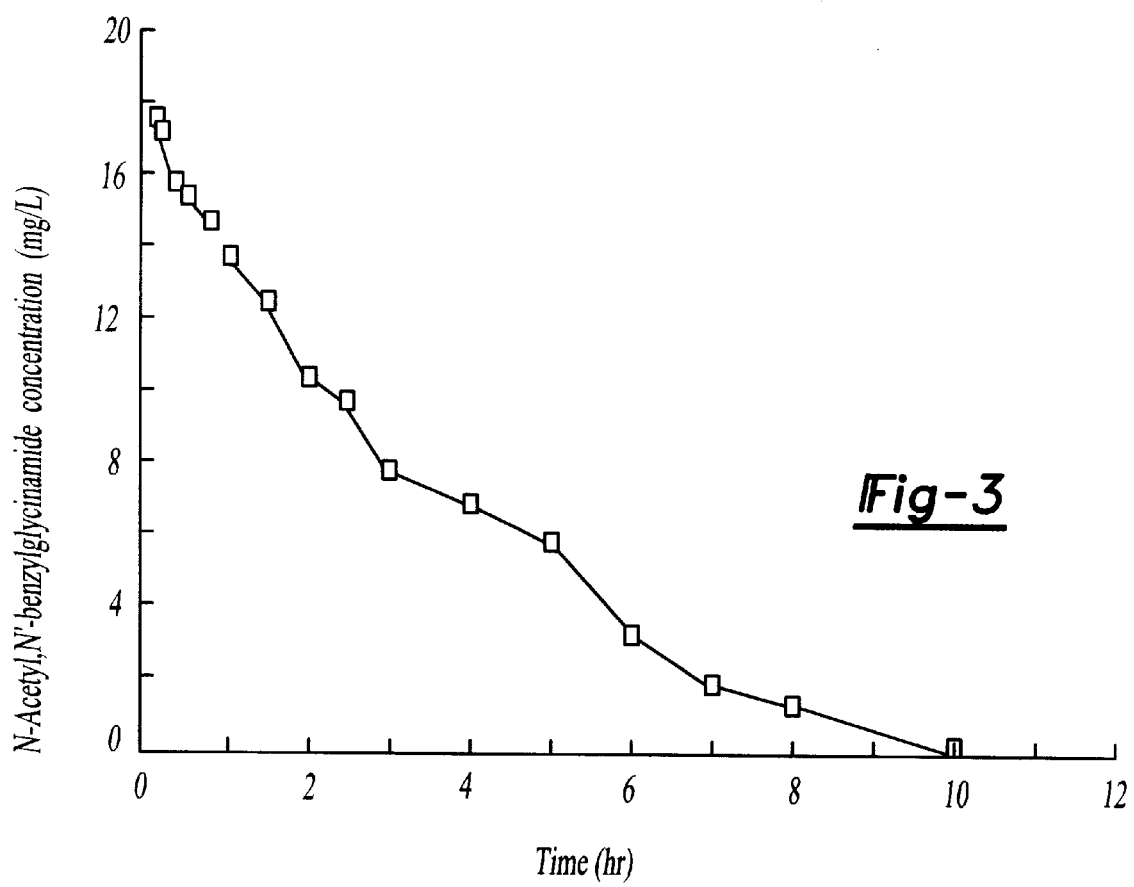
FIG. 3 is a graph showing the mean plasma levels of N-benzyloxycarbonylglycine (VIII) following its iv administration to six dogs.

Z-glycinamide (IX) was mainly metabolized to Z-glycine (VIII) (FIG. 2). Therefore, the pharmacokinetics of Z-glycine was investigated following its iv administration to the same dogs (FIG. 3) in order to calculate the fraction metabolized ($f_m$) of Z-glycinamide to Z-glycine. The mean $f_m$ values was 80±14%.

Table 3 describes the mean pharmacokinetic parameters of compounds VII, VIII and IX in comparison to that of phthaloyl glycinamide and valproyl glycinamide (TV 1901).

Example 2

Studies in rats demonstrated that N-benzyloxycarbonylglycinamide (Z-glycinamdie; IX) crossed the blood-brain-barrier more readily than does Z-glycine (VIII; control). In two separate experiments cold (unlabeled) Z-glycinamdie and Z-glucine were injected intravenously to male rats. For the experiments, the two compounds were dissolved in 0.2 mL of DMSO and were injected at a dose of 25 mg. Blood samples (8 mL each) were collected from the ascending vena cava of an individual rat at 5, 10, 20, 30, 45, 60, 90, 120, 150, 180, 240, 300, 360 and 480 minutes after administering the drug dose. Three rats were sacrificed for each of the aforementioned time measurements and the plasma or tissue obtained from each rat for each time point was averaged. Plasma was immediately separated by centrifugation at 3000 g for 15 minutes and stored at -20° C. until analyzed. Brain and liver were quickly removed at the same time intervals under light ether anesthesia, the excised tissues were immersed in liquid nitrogen for a few minutes and stored at -70° C. until analyzed. Four rats were kept in metabolic cages and the cumulative urine was collected from each rat for 480 minutes after dosing.

Studies as set forth herein above analyzed the metabolism of N-benzyloxycarbonylglycinamide (IX) in rats occurs primarily in the liver, as in the dog studies. In rats 75% of the N-benzyloxycarbonylglycinamide (IX) dose administered is metabolized to Z-glycine and excreted in the urine with the remaining 15% excreted as N-benzyloxycarbonylglycinamide (IX).

Throughout this application, various publications, including United States patents, are referenced. Full citations for the non-patent publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

$NH_2CH_2$—CO—$NHCH_2$—COX
X = OH    Glycylglycine (I)
X = $NH_2$   Glycylglycinamide (II)
$NH_2(CH_2)_3$—CO—$NHCH_2$—$CONH_2$
Gaboylglycinamide (III)
$CH_3$—CO—$NHCH_2$—COX
X = OH    N-acetylglycine (IV)
X = $NH_2$   N-Acetylglycinamide (V)
$CH_3$—CO—$NHCH_2$—CO—$NHCH_2$—$CONH_2$
N-Acetylglycylglycinamide (VI)

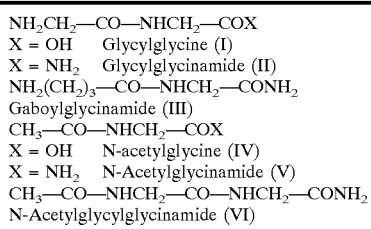

N-Acetyl,N'-benzylglycinamide (VII)

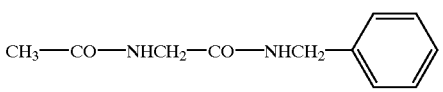

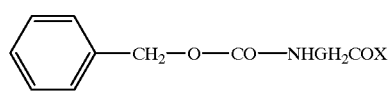

X = OH    N-Benzyloxycarbonylglycine-Z-glycine (VIII)
X = $NH_2$   N-Benzyloxycarbonylglycinamide-Z-glycinamide (IX)

TABLE 1-continued

X = OH  N-Benzyloxycarbonylglycine-Z-glycylglycine (X)
X = NH₂  N-Benzyloxycarbonylglycylglycinamide-Z-glycylglycinamide (XI)

TABLE 2

Anticonvulsant activity and neurotoxicity of N-acetyl, N'-benzylglycinamide (VII) and N-benzyloxycarbonylglycinamide (IX) following ip administration to mice in comparison to phthaloylglycinamide and N-valproylglycinamide[a].

| valproyl | N-acetyl, N'-benzylglycin-amide | Z-glycin-amide | phthaloyl glycin-amide | glycin-amide |
|---|---|---|---|---|
| MES, $ED_{50}$ (mg/kg) | 88 | 46 | 94 | 152 |
| sc Met, $ED_{50}$ (mg/kg) | — | 95 | >400 | 127 |
| Neurotoxicity, $TD_{50}$ (mg/kg) | >200 | 230 | >600 | 369 |
| PI, MES | 2.3 | 5.0 | >64 | 2.4 |
| PI, sc Met | — | 2.4 | — | 2.9 |

MES - Maximal electroshock.
sc Met- Chemically induced shock obtained following subcutaneous injection of metrazole.
$ED_{50}$ - Effective dose in 50% of the test animals.
$TD_{50}$ - Neurotoxic dose in 50% of the test animals.
PI - Protective index- The ratio of the $TD_{50}$ to the $ED_{50}$.
[a]The data for phthaloylglycinamide and valproylglycinamide are taken from Salach, et al (1994) and Hadad and Bialer (1995), respectively.

TABLE 3

Mean pharmacokinetic parameters of N-acetyl, N'-benzyl glycinamide (VII), N-benzyloxycarbonylglycinamide (IX), N-benzyloxycarbonylglycine (VIII), phthaloylglycinamide and N-valprolglycinamide obtained following iv administration to dogs.

| Pharmacokinetic valproyl parameters | N-acetyl, N'-benzylglycin-amide | Z-glycin-amide | phthaloyl glycin-amide[a] | glycin-amide[b] |
|---|---|---|---|---|
| $t_{1/2}$ hr | 2.1 ± 0.4 | 2.3 ± 1.3 | 3.4 ± 0.7 | 2.7 ± 0.5 |
| CL (L/hr) | 6.4 ± 1.4 | 11 ± 3 | 9 ± 2 | 3 ± 0.8 |
| $V_{ss}$ (L) | 20 ± 4 | 33 ± 10 | 46 ± 13 | 12 ± 3 |
| $V_{\beta}$ (L) | 19 ± 6 | 33 ± 10 | 48 ± 13 | 11 ± 3 |
| MRT (hr) | 3.3 ± 0.8 | 3.3 ± 1.8 | 4.6 ± 0.9 | 4.6 ± 0.7 |
| fe (%) | 9.8 ± 5.4 | 2.3 ± 1.3 | 7.0 ± 0.7 | 8.4 ± 2.6[c] |

| Pharmacokinetic parameter | Z-glycine |
|---|---|
| $t_{1/2}$ hr | 0.6 ± 0.14 |
| CL (L/hr) | 5.4 ± 0.5 |
| $V_{ss}$ (L) | 4.9 ± 0.6 |
| $V_{\beta}$ (L) | 4.5 ± 0.8 |
| MRT (hr) | 0.8 ± 0.1 |
| fe (%) | 48 ± 1.2 |
| fm (%)[d] | 80.1 ± 13.6 |
| Mu/D (%)[e] | 20 ± 19.8 |

[a]The data from Salach et al, 1994.
[b]N-valproylglycinamide was given at a dose equivalent to 400 mg of valproic acid. The data from Hadad and Bialer, 1995
[c]New data which are not from Hadad and Bialer, 1995
[d]Fraction metabolized of Z-glycinamide to Z-glycine.
[e]Mu/D The fraction of Z-glycine excreted in the urine as a metabolite of Z-glycinamide.

REFERENCES

Benet and Galeazzi (1979). Non-compartmental determination of steady-state volume of distribution. J. Pharm. Sci. 68:1071–1074.

Bialer, et al (1996a). Progress report on new antiepileptic drugs a summary of the Third Eilat Conference. Epilepsy Res. 25:299–319.

Bialer, et al (1996b). Pharmacokinetic analysis and antiepileptic activity of tetramethylcyclopropane analogous of valpromide. Pharm. Res. 13:284–289.

Capobianco et al (1996). An overview of the diagnosis and pharmacologic treatment of migraine. May Clin Proc 71:1055–66.

Chadwick (ed). New Trends in Epilepsy Management: The Role of Gabapentin. Royal Society of Medicine Services Ltd., London, 1993.

Clark, et al (1995). Remacemide hydrochloride in R. H. Levy, R. H. Mattson and B. S. Meldrun (eds.) Antiepileptic Drugs, 4th ed. Raven Press, pp. 1035–1044.

Conley and Kohn (1987). Functionalized DL-amino acid derivatives. Potent new agent for the treatment of epilepsy. J. Med. Chem. 30:567–574.

Dreifuss (1987). New anticonvulsant drugs in *Epilepsy, Progress in Treatment,* M. Dam. S. I. Johannessen, B. Nilsson and M. Sillapaa (eds.), Wiley & Sons, N.Y., pp. 247–256.

Freed, et al (1979). Anticonvulsant properties of betaine. Epilepsia. 20:209–213.

Freed (1985). Prevention of strychnine-induced seizures and deaths by the N-methylated glycine derivatives betaine, dimethylglycine and sarcosine. Pharmacol. Biochem. Behav. 22:641–643.

"GABA in Nervous System Function", E. Roberts, T. N. Chase, D. B. Tower (eds.), Raven Press, N.Y. (1976).

Garcia and Altman (1997). Chronic pain states: Pathophysiology and medical therapy. Semin Arthritis Rheum 27:1–16.

Gibaldi and Perrier (1982). Pharmacokinetics, Ed. 2, Marcel Dekker, New York, pp. 445–449.

Gidal et al (1996). Current developments in neurology, Part I: Advances in the pharmacotherapy of headache, epilepsy and multiple sclerosis. Ann Pharmacother 30(11):1272–6.

Gonzales (1995). Central pain: Diagnosis and treatment strategies. Neurology 45(12 Suppl 9):S11-6; Discussion S35-6.

Guay (1995). The emerging role of valproate in bipolar disorder and other psychiatric disorders. Pharmacotherapy 15(5):631–47.

Hadad and Bialer (1995). Pharmacokinetic analysis and antiepileptic activity of N-valproyl derivatives of GABA and glycine. Pharm. Res. 12, 905–910.

Hadad and Bialer (1997). Pharmacokinetic analysis and antiepileptic activity of two new isomers of N-valproyl glycinamide. Biopharm. Drug Disposit. 18:557–556.

Kohn, et al (1988). Marked stereospecificity in a new class of anticonvulsants. Brain Res. 457:371–375.

Kohn, et al (1990). Preparation and anticonvulsant activity of a series of functionalized aromatic and heteroaromatic amino acids. J. Med. Chem. 33:919–926.

Kohn, et al (1991). Preparation and anticonvulsant activity of a series of functionalized heteroatom-substituted amino acids. J. Med. Chem. 34, 2444–2542.

Krogsgaard-Larsen, et al (1988). Recent advances in GABA agonists, antagonists and uptake inhibitors: Structure activity relationships and therapeutic potential. Advanc. Drug. Res. 17:382–456.

Lambert, et al (1994). Anticonvulsant activities of N-benzyloxycarbonylglycine after parenteral administration. Neuroreport. 5:777–780.

Lambert, et al (1996). Anticonvulsant activity of ester- and amide-type lipid conjugates of glycine and N-benzyloxycarbonylglycine. Eur. J. Pharm. Sci. 4:159–166.

Liu, et al (1990). Potentiation of γ-vinyl GABA (vigabatrin) effects by glycine. Eur. J. Pharmacol. 182:109–115.

McQuay, et al (1995). Anticonvulsant drugs for management of pain: A systemic review. BMJ 311(7012):1047–52.

Mielke (1994). Anticonvulsant therapy for mood disorders. South Med J 87(7):685–8.

Mumford and Canon (1994). Vigabatrin. Epilepsia 35 (Suppl. 5) S25–S27.

Peterson, et al (1990). Potentiation by glycine of anticonvulsant drugs in maximal electroshock seizures in rats. Neuropharmacology, 29:392–409 (1990).

Porter, et al (1984). Antiepileptic drug development program. Cliv. Clin. Quarter. 51:293–305.

Porter (1986). Antiepileptic drugs: efficacy and inadequacy in *New Anticonvulsant Drugs,* B. S. Meldrum and R. J. Porter (eds.), Libbey, London, pp. 3–16.

Post et al (1996). The place of anticonvulsant therapy in bipolar illness. Psychopharmacology (Berl) 128(2):115–29.

Puzantian (1996). Criteria for use of valproate in adult psychiatric inpatients and outpatients. Am J Health Syst Pharm 53(10):1187–8.

Roba et al (1986). Milacemide in "New Anticonvulsant Drug", B. S. Meldrum and R. J. Porter (eds.), Jhon Libny, London, pp. 179–190.

Sachs (1996). Bipolar mood disorder: Practical Strategies for acute and maintenance phase treatment. J Clin Psychopharmacol 16(2 Suppl 1):32S–47S.

Salach, et al (1994). Comparative pharmacokinetic and pharmacodynamic analysis of phthaloyl glycine derivatives with potential antiepileptic activity. Pharm. Res. 11:1424–1434.

Seiler and Sarhan (1984). Synergistic anticonvulsant effects of a GABA agonist and glycine. Gen. Pharmacol. 15:367–369.

Silberstein and Lipton (1994). Overview of diagnosis and treatment of migraine. Neurology 44(10 Suppl 7):S6–16.

Swerdlow (1984). Anticonvulsant drugs and chronic pain. Clin Neuropharmacol 7(1):51–82.

Toth and Lajtha (1984). Glycine potentiates the action of some anticonvulsant drugs in some seizure models. Neurochem. Res. 8:1711–1718.

VanValkenburg et al (1992). New uses of anticonvulsant drugs in psychosis. Drugs 44(3):326–35.

Wood, et al (1988). Amplification by glycine of the effect of the GABA transport inhibitor THPO on synaptosomal GABA level. Neurochem. Res. 13:917–921.

Yamaoka, et al (1978). Statistical moments in pharmacokinetics. J. Pharmacokinet. Biopharm. 6:547–558.

Yamaoka (1986). Methods for pharmacokinetic analysis for personal computers. Edition 2, Nanko-D Led., Tokyo, pp. 145–175.

What is claimed is:

1. An anticonvulsant compound N-benzyloxycarbonylglycinamide-Z-glycinamide.

2. An anticonvulsant pharmaceutical composition for administering to a mammal comprising an effective amount of an active ingredient as set forth in claim 1 and a pharmaceutically acceptable carrier or diluent.

3. A method of controlling epileptic seizures in a mammal in need of such treatment by administering to the mammal an effective amount of the composition as set forth in claim 2.

4. A method of controlling febrile convulsions in a mammal in need of such treatment by administering to the mammal an effective amount of the composition as set forth in claim 2.

5. A method of controlling convulsions precipitated by an irritative lesion in the brain in a mammal by administering to the mammal an effective amount of the composition as set forth in claim 2.

6. The composition as set forth in claim 2 wherein said mammal is a human patient in need of such control.

* * * * *